(12) United States Patent
Wang et al.

(10) Patent No.: US 9,065,144 B2
(45) Date of Patent: Jun. 23, 2015

(54) ELECTRODE INCLUDING A 3D FRAMEWORK FORMED OF FLUORINATED CARBON

(75) Inventors: Francis Wang, Minneapolis, MN (US); Joseph E. Sunstrom, Newark, DE (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 260 days.

(21) Appl. No.: 13/205,772

(22) Filed: Aug. 9, 2011

(65) Prior Publication Data

US 2012/0041507 A1  Feb. 16, 2012

Related U.S. Application Data

(60) Provisional application No. 61/373,094, filed on Aug. 12, 2010.

(51) Int. Cl.
*H01M 10/04* (2006.01)
*H01M 2/02* (2006.01)
*H01M 4/583* (2010.01)
(Continued)

(52) U.S. Cl.
CPC .......... *H01M 10/049* (2013.01); *Y10T 29/4911* (2015.01); *Y10T 29/49108* (2015.01); *A61N 1/378* (2013.01); *H01M 2/027* (2013.01);
(Continued)

(58) Field of Classification Search
CPC ............................ H01M 2/027; H01M 10/049
USPC ........................ 607/36; 429/235, 231.7, 231.8
See application file for complete search history.

(56) References Cited

U.S. PATENT DOCUMENTS 4,217,939 A   8/1980  Yanagihara et al.
4,791,791 A * 12/1988  Flegal et al. .................. 62/55.5
(Continued)

FOREIGN PATENT DOCUMENTS

EP   1243680 A2 *  9/2002
EP   1555244 A2    7/2005
(Continued)

OTHER PUBLICATIONS

"U.S. Appl. No. 13/584,057 , Response filed Sep. 23, 2013 to Non Final Office Action mailed Jun. 21, 2013", 7 pgs.
(Continued)

*Primary Examiner* — Catherine Voorhees
(74) *Attorney, Agent, or Firm* — Schwegman Lundberg & Woessner, P.A.

(57) ABSTRACT

One example includes a battery case sealed to retain electrolyte, an electrode disposed in the battery case, the electrode comprising a framework defining open areas disposed along three axes ("3D framework") formed of fluorinated carbon including elements that each include a conductive core at least partially surrounded by an electrochemically active portion, wherein a plurality conductive cores form an electrically conductive network, a conductor electrically coupled to the electrode in electrical communication with the conductive network and sealingly extending through the battery case to a terminal disposed on an exterior of the battery case, a further electrode disposed in the battery case, a separator disposed between the electrode and the further electrode and a further terminal disposed on the exterior of the battery case and in electrical communication with the further electrode, with the terminal and the further terminal electrically isolated from one another.

19 Claims, 9 Drawing Sheets

(51) Int. Cl.
*H01M 4/64* (2006.01)
*A61N 1/378* (2006.01)
*H01M 10/052* (2010.01)

(52) U.S. Cl.
CPC ............... *H01M4/583* (2013.01); *H01M 4/64* (2013.01); *H01M 10/052* (2013.01)

(56) References Cited

U.S. PATENT DOCUMENTS

| | | | |
|---|---|---|---|
| 5,116,592 A * | 5/1992 | Weinberg | 423/415.1 |
| 5,512,390 A | 4/1996 | Obushenko | |
| 5,589,301 A | 12/1996 | Edgington et al. | |
| 5,728,490 A | 3/1998 | Edgington et al. | |
| 5,738,907 A | 4/1998 | Vaccaro et al. | |
| 5,798,033 A | 8/1998 | Uemiya et al. | |
| 5,898,564 A | 4/1999 | Mayer et al. | |
| 6,068,921 A * | 5/2000 | Yamana et al. | 428/402 |
| 6,351,371 B1 | 2/2002 | Yoshida et al. | |
| 6,498,951 B1 * | 12/2002 | Larson et al. | 607/36 |
| 6,605,390 B1 * | 8/2003 | Moore et al. | 429/231.8 |
| 6,645,667 B1 * | 11/2003 | Iwamoto et al. | 429/126 |
| 6,783,888 B2 | 8/2004 | Gan et al. | |
| 6,801,424 B1 | 10/2004 | Nielsen et al. | |
| 6,885,545 B2 | 4/2005 | Michel et al. | |
| 6,979,513 B2 * | 12/2005 | Kelley et al. | 429/121 |
| 7,060,391 B2 | 6/2006 | Gyenge et al. | |
| 7,341,806 B2 | 3/2008 | Kelley et al. | |
| 7,377,948 B2 | 5/2008 | Faris | |
| 7,563,542 B2 | 7/2009 | Yazami et al. | |
| 2001/0020319 A1 | 9/2001 | Farahmandi et al. | |
| 2003/0036001 A1 | 2/2003 | James et al. | |
| 2004/0147960 A1 | 7/2004 | O'Phelan et al. | |
| 2006/0166078 A1 * | 7/2006 | Chen et al. | 429/62 |
| 2007/0156197 A1 * | 7/2007 | Root et al. | 607/36 |
| 2007/0248887 A1 | 10/2007 | Eskra et al. | |
| 2010/0010562 A1 | 1/2010 | Daley et al. | |
| 2010/0055571 A1 | 3/2010 | Le Guenne et al. | |
| 2010/0246100 A1 | 9/2010 | Umemoto et al. | |
| 2010/0259866 A1 | 10/2010 | Shaffer et al. | |
| 2010/0323244 A1 * | 12/2010 | Chiang et al. | 429/220 |
| 2011/0005065 A1 | 1/2011 | Chiang et al. | |
| 2011/0033747 A1 | 2/2011 | Phillips et al. | |
| 2011/0052994 A1 | 3/2011 | Harada et al. | |
| 2011/0111303 A1 | 5/2011 | Kung et al. | |
| 2011/0152958 A1 | 6/2011 | Sherwood et al. | |
| 2011/0152959 A1 | 6/2011 | Sherwood | |
| 2012/0078317 A1 | 3/2012 | Wang et al. | |
| 2013/0041420 A1 | 2/2013 | Sherwood | |

FOREIGN PATENT DOCUMENTS

| | | |
|---|---|---|
| WO | WO-0157928 A1 | 8/2001 |
| WO | WO-2011075506 A2 | 6/2011 |
| WO | WO-2013022666 A2 | 2/2013 |
| WO | WO-2013022666 A3 | 4/2013 |

OTHER PUBLICATIONS

"U.S. Appl. No. 13/564,057, Non Final Office Action mailed Jun. 21, 2013", 6 pgs.

"International Application Serial No. PCT/US2012/049132, International Preliminary Report on Patentability mailed Aug. 19, 2013", 14 pgs.

"International Application Serial No. PCT/US2012/049132, International Search Report mailed Feb. 6, 2013", 3 pgs.

"International Application Serial No. PCT/US2012/049132, International Written Opinion mailed Feb. 6, 2013", 7 pgs.

"U.S. Appl. No. 13/205,757, Non Final Office Action mailed May 8, 2014", 12 pgs.

"U.S. Appl. No. 13/205,757, Response filed Jan. 21, 2014 to Restriction Requirement mailed Dec. 23, 2013", 6 pgs.

"U.S. Appl. No. 13/205,757, Restriction Requirement mailed Dec. 23, 2013", 8 pgs.

"U.S. Appl. No. 13/564,057, Non Final Office Action mailed Feb. 14, 2014", 12 pgs.

"U.S. Appl. No. 13/564,057, Response filed May 14, 2014 to Non Final Office Aciton mailed Feb. 14, 2014", 8 pgs.

"U.S. Appl. No. 13/205,757, Final Office Action mailed Dec. 11, 2014", 15 pgs.

"U.S. Appl. No. 13/205,757, Response filed Aug. 7, 2014 to Non Final Office Action mailed May 8, 2014", 11 pgs.

"U.S. Appl. No. 13/564,057, Advisory Action mailed Sep. 25, 2014", 3 pgs.

"U.S. Appl. No. 13/564,057, Appeal Brief filed Dec. 22, 2014", 12 pgs.

"U.S. Appl. No. 13/564,057, Final Office Action mailed Jun. 23, 2014", 10 pgs.

"U.S. Appl. No. 13/564,057, Response filed Aug. 21, 2014 to Final Office Action mailed Jun. 23, 2014", 8 pgs.

* cited by examiner

ELECTRODE INCLUDING A 3D FRAMEWORK FORMED OF FLUORINATED CARBON

CROSS-REFERENCE TO RELATED APPLICATIONS

This application claims the benefit of U.S. Provisional Application No. 61/373,094, filed on Aug. 12, 2010, under 35 U.S.C. §119(e), which is incorporated herein by reference in its entirety.

TECHNICAL FIELD

This document relates generally to energy storage and particularly to an electrode including a 3D framework formed of fluorinated carbon.

BACKGROUND

Some electrochemically active battery materials offer superior energy density, but are difficult to implement in a battery using traditional battery manufacturing structures and materials. Specifically, some battery manufacturing structures and methods can render certain battery chemistries less effective. Structures and methods that enable using new battery chemistries would be beneficial.

SUMMARY

One example includes a battery case sealed to retain electrolyte, an electrode disposed in the battery case, the electrode including a framework defining open areas disposed along three axes ("3D framework") formed of fluorinated carbon including elements that each include a conductive core at least partially surrounded by an electrochemically active portion, wherein a plurality conductive cores form an electrically conductive network, a conductor electrically coupled to the electrode in electrical communication with the conductive network and sealingly extending through the battery case to a terminal disposed on an exterior of the battery case, a further electrode disposed in the battery case, a separator disposed between the electrode and the further electrode and a further terminal disposed on the exterior of the battery case and in electrical communication with the further electrode, with the terminal and the further terminal electrically isolated from one another.

Example 2 includes the subject matter of example 1, wherein the active portion includes fluorinated carbon with a formula CFx in which x is in the range of from about 0.5 to about 0.95.

Example 3 includes the subject matter of any of examples 1-2, herein the 3D framework is formed of carbon foam that is vitreous.

Example 4 includes the subject matter of example 3, wherein the active portion includes solid-gas fluorinated carbon.

Example 5 includes the subject matter of any of examples 1-4, wherein the 3D framework includes a carbon foam defining open cells.

Example 6 includes the subject matter of example 5, wherein the carbon foam is around 40% porous.

Example 7 includes the subject matter of any of examples 1-6, wherein the carbon foam is flexible.

Example 8 includes the subject matter of example 7, wherein the electrode includes a reticulated vitreous carbon foam.

Example 9 includes the subject matter of any of examples 1-8, wherein the electrode is substantially free of binders.

Example 10 includes the subject matter of example 9, wherein the electrode is substantially free of carbon additives binders.

An eleventh example includes a hermetically sealed device housing, a battery disposed in the hermetically sealed device housing, the battery that includes a battery case sealed to retain electrolyte, an electrode disposed in the battery case, the electrode including a framework defining open areas disposed along three axes ("3D framework") formed of fluorinated carbon including elements that each include a conductive core at least partially surrounded by an electrochemically active portion, wherein a plurality conductive cores form an electrically conductive network, a conductor electrically coupled to the electrode and sealingly extending through the battery case to a terminal disposed on an exterior of the battery case, a further electrode disposed in the battery case, a separator disposed between the electrode and the further electrode and a further terminal disposed on the exterior of the battery case and in electrical communication with the further electrode, with the terminal and the further terminal electrically isolated from one another and an electronic cardiac rhythm management circuit coupled to the battery and adapted to discharge the battery to provide a therapeutic pulse.

Example 12 includes the subject matter of example 11, wherein the device housing has a form factor, and the battery case is shaped to at least partially conform to the form factor.

Example 13 includes the subject matter of example 12, wherein the battery case has a case shape, and the electrode is shaped to at least partially mate the case shape.

A fourteenth example includes forming a battery electrode by fluorinating elements of a carbon framework defining open areas disposed along three axes to form a fluorinated carbon framework defining open areas disposed along three axes ("3D framework") including an electrochemically active portion and an electrical network of conductive portions, stacking the battery electrode into a battery stack with other electrodes, disposing the battery stack in a battery case, connecting the electrodes of the battery stack to terminals for coupling to electronics, filling the battery case with electrolyte and sealing the battery case.

Example 15 includes the subject matter of example 14, wherein the electrochemically active portion has a formula CFx in which x is in the range of from about 0.5 to about 0.95.

Example 16 includes the subject matter of example 14, wherein fluorinating elements of a carbon framework defining open areas disposed along three axes includes fluorinating open cells of a carbon foam.

Example 17 includes the subject matter of example 16, wherein the carbon foam is around 40% porous.

Example 18 includes the subject matter of any of examples 14-17, further including excising the battery electrode into a shaped electrode.

Example 19 includes the subject matter of example 18, further including masking the electrode to define a masked portion, wherein connecting the electrodes of the battery stack to terminals for coupling to electronics includes connecting the electrodes via the masked portion.

Example 20 includes the subject matter of example 14, further including stacking the other electrodes into the stack such that the stack has a predetermined energy density.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Examples discussed here relate to electrochemical batteries including lithium. In some instances, the anode (or negative electrode) is formed from lithium. In certain examples, a cathode (or positive electrode) is constructed of a mass formed of carbon. The mass includes a framework defining open areas disposed along three axes, (as used herein, a "3D framework"). For example, an opening is bounded by edges defining the opening along three axes. The edges defining the opening define planes enclose the opening on all sides. The 3D framework includes a conductive carbon portion that serves as a current collector, in certain instances. The 3D framework also includes, but is not limited to, a fluorinated carbon portion that serves as an active material, in some examples. In some instances, the conductive carbon portion is interior to the fluorinated carbon portion. The conductive carbon portion and the fluorinated carbon portion are formed from the same starting material, a carbon framework defining open areas disposed along three axes, in some instances. Some instances relate to a lithium primary battery.

$Li/MnO_2$ battery systems, such as those operating at or around 3.0V, can be improved upon. The present subject matter addresses at least one problem with these battery systems: the energy density of $Li/MnO_2$ batteries is difficult to increase, due to the capacity of $MnO_2$ and its maximum loading level. Loading level refers to the amount of active material per unit area (i.e., g/cm2). $CF_x$ batteries provide an opportunity to improve energy density, but existing $CF_x$ designs have drawbacks.

$CF_x$ chemistry has an energy density of around 1.5 times that of $MnO_2$. However, $CF_x$ electrodes are difficult to process in the form of a coated or pelletized electrode. For example, at the end of the discharge of a $Li/CF_x$ battery, the cathode can expand by as much as two to three times, limiting full utilization of the $CF_x$ energy density.

To address inefficiencies that result from the poor electronic conductivity of $CF_x$, some designs use a high percentage of conductive additives, such as acetylene black carbon, to achieve an acceptable level of electronic conductivity. Some of these designs have a porous (e.g., >50% porous) electrode with poor volumetric capacity as a result of the poor tap density of acetylene black carbon. While increasing the size of current collectors addresses certain aspects of the problem, a size increase is not sufficient, as portions of the current collector still fail to adequately conduct with parts of the electrochemically active area of the $CF_x$. Further, size increases are undesirable in implantable devices, as increased size leads to patient discomfort.

Despite these issues, the $Li/CF_x$ chemistry is desirable. $CF_x$ batteries feature high volumetric capacity. $CF_x$ batteries have desirable long term stability. Some have less than one percent self discharge per year, for example. $CF_x$ batteries have desirable voltage characteristics. Some have an open circuit voltage of around 3.2 volts, for example. Some have a closed circuit voltage of around 2.5 to 2.7 volts, for example. $CF_x$ batteries additionally have predictable low to medium rate performance.

Because $CF_x$ offers these benefits, various examples provide an electrode formed of a 3D framework including a non-fluorinated carbon current collector interior, with an exterior portion that is fluorinated forming active material. The interior is electrically conductive. The interior together with active material comprises a cathode, in various examples. Various examples provide a cathode that addresses the above inefficiencies to provide a $CF_x$ battery that discharges well and has an improved energy density. In certain examples, the 3D framework is formed of carbon foam. In certain examples, the 3D framework is porous. Additional 3D frameworks include, but are not limited to, fluorinated carbon fabrics, thatches, braids, scaffolding, skeleton, fins, tendrils and the like. The 3D framework examples disclosed here include features that can be used in combination, that is, aspects from one 3D framework are combinable aspects from another 3D framework, in various examples.

Figure 1:
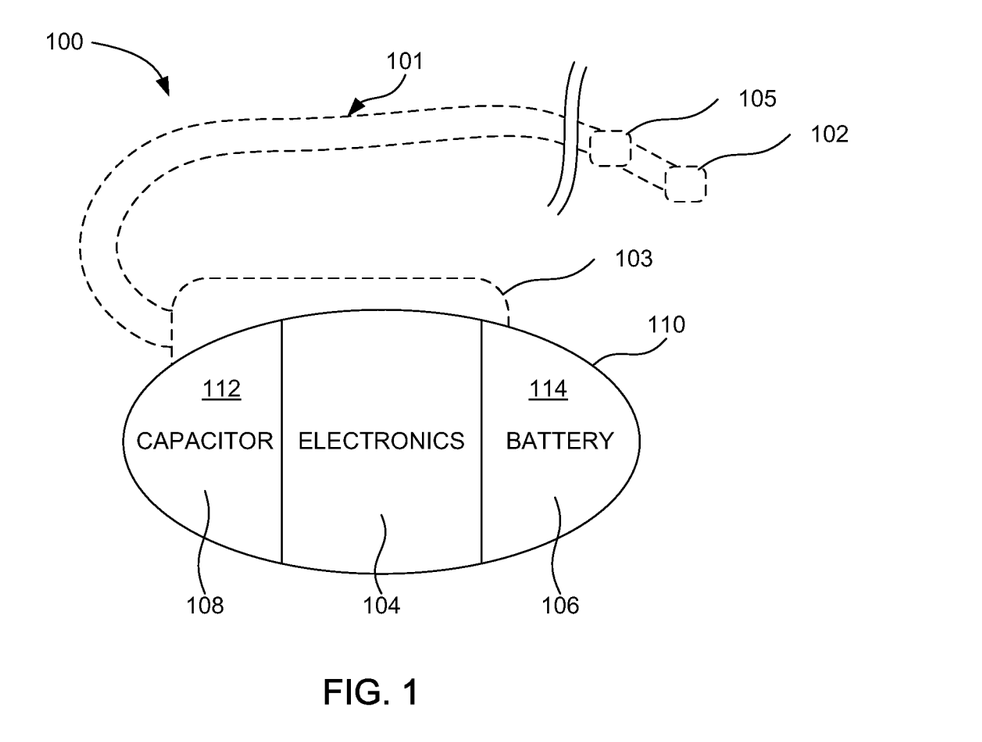
FIG. 1 is a schematic of a medical system including a battery that includes a fluorinated carbon framework defining open areas disposed along three axes, according to some embodiments.

FIG. 1 is a schematic of a medical system including a battery that includes a fluorinated carbon 3D framework, according to certain examples. The system 100 represents any number of systems to provide therapeutic stimulus, such as to a heart. Examples of medical systems include, but are not limited to, implantable pacemakers, implantable defibrillators, implantable nerve stimulation devices and devices that provide stimulation from outside the body, including, but not limited to, external defibrillators.

In various examples, electronics 104 are to monitor the patient, such as by monitoring a sensor 105, and to monitor and control activity within the system 100. In some examples, the electronics 104 are to monitor a patient, diagnose a condition to be treated such as an arrhythmia, and control delivery of a stimulation pulse of energy to the patient. In some instances, electronics 104 are powered wirelessly using an inductor. In additional configurations, the electronics 104 are powered by a battery 106. In some examples, electronics 104 are to direct small therapeutic bursts of energy from the battery 106 to a patient.

For therapies that use energy discharge rates exceeding what battery 106 is able to provide, such as defibrillation, a capacitor 108 is used. Energy from the battery 106 is controlled by the electronics 104 to charge the capacitor 108. The capacitor 108 is controlled with the electronics 104 to discharge to a patient to treat the patient. In certain examples, the capacitor 108 completely discharges to a patient, and in additional examples is switched on to provide therapeutic energy and switched off to truncate therapy delivery.

Some instances of a system 100 include an optional lead system 101. In certain instances, after implantation, the lead system 101 or a portion of the lead system 101 is in electrical communication with tissue to be stimulated. For example, some configurations of lead system 101 contact tissue with a stimulation electrode 102. The lead system 101 couples to other portions of the system 100 via a connection in a header 103. Examples of the system 101 use different numbers of stimulation electrodes and/or sensors in accordance with the needs of the therapy to be performed.

Additional examples function without a lead 101 and are leadless. Leadless examples are positioned in contact with the tissue to be stimulated, or are positioned proximal to a tissue to be stimulated to shock the tissue through intermediary tissue. In certain examples, leadless systems are easier to implant and are less expensive as they do not use additional lead components. The housing 110 is used as an electrode in leadless configurations, in certain examples.

In certain examples, the electronics 104 include an electronic cardiac rhythm management circuit coupled to the battery 106 and the capacitor 108 to discharge the capacitor 108 to provide a therapeutic defibrillation pulse. In some instances, the system 100 includes an anode and a second electrode such as a cathode sized to deliver a defibrillation pulse of at least approximately 50 joules. This energy level is predetermined to achieve a delivered energy level mandated by a governing body or standard associated with a geographic region, such as a European country. In an additional example, the anode and second electrode are sized to deliver a defibrillation pulse of at least approximately 60 joules. This energy level is predetermined to achieve an energy level mandated by a governing body of another region, such as the United States. In some instances, electronics 104 are to control discharge of a defibrillation pulse so that the medical system 100 delivers only the energy mandated by the region in which the system 100 is used.

In certain examples, the battery 106 includes a battery case 114 sealed to retain electrolyte. In certain examples, the battery case 114 is welded. In some instances, the battery case 114 is hermetically sealed. In additional examples, the battery case 114 is sealed to retain electrolyte, but is sealed with a seal to allow flow of other matter, such as gaseous diatomic hydrogen or a helium molecule. Some of these examples use an epoxy seal. Several materials can be used to form battery case 114, including, but not limited to, aluminum, titanium, stainless steel, nickel, a polymeric material, or combinations of these materials. The battery case 114 is sealed to retain electrolyte. The battery case 114 includes a seal, such as a resin based seal including but not limited to epoxy, in certain examples. Certain examples include a rubber seal to seal multiple case portions to one another, or to seal subcomponents such as a feedthrough to one or more case portions. In certain examples, the battery case 114 is welded together from subcomponents. Some instances include a case that includes one or more backfill ports, but the present subject matter is not so limited.

In certain examples, the capacitor 108 includes a capacitor case 112 sealed to retain electrolyte. In some instances, the capacitor case 112 is welded. In some instances, the capacitor case 112 is hermetically sealed. In additional examples, the capacitor case 112 is sealed to retain electrolyte, but is sealed with a seal to allow flow of other matter, such as gaseous diatomic hydrogen or a helium molecule. Some of these examples use an epoxy seal. Several materials can be used to form capacitor case 112, including, but not limited to, aluminum, titanium, stainless steel, nickel, a polymeric material, or combinations of these materials. The capacitor case 112 is sealed to retain electrolyte. Various electrolytes can be used including, but not limited to, Suzuki-Techno Corporation electrolyte model 1184. The capacitor case 112 includes a seal, such as a resin based seal including but not limited to epoxy, in certain examples. Some instances include a rubber seal to seal multiple case portions to one another, or to seal subcomponents such as a feedthrough to one or more case portion. In some instances, the capacitor case 112 is welded together from subcomponents. Certain examples include a case that includes one or more backfill ports, but the present subject matter is not so limited.

A hermetically sealed device housing 110 is used to house components, such as the battery 106, the electronics 104, and the capacitor 108. Hermeticity is provided by welding components into the hermetically sealed device housing 110 in certain examples. Other examples bond portions of the housing 110 together with an adhesive such as a resin based adhesive such as epoxy. Accordingly, some examples of the housing 110 include an epoxy sealed seam or port. Several materials can be used to form housing 110, including, but not limited to, titanium, stainless steel, nickel, a polymeric material, or combinations of these materials. In various examples, the housing 110 and the case 112 are biocompatible.

The battery 106 is improved by the present electrode technology in part because it can be made smaller. In certain examples, it is manufacturable with less expense. The improvement provided by these electrodes is pertinent to any application where high-energy, high-voltage, or space-efficient batteries are desirable.

Figure 2:
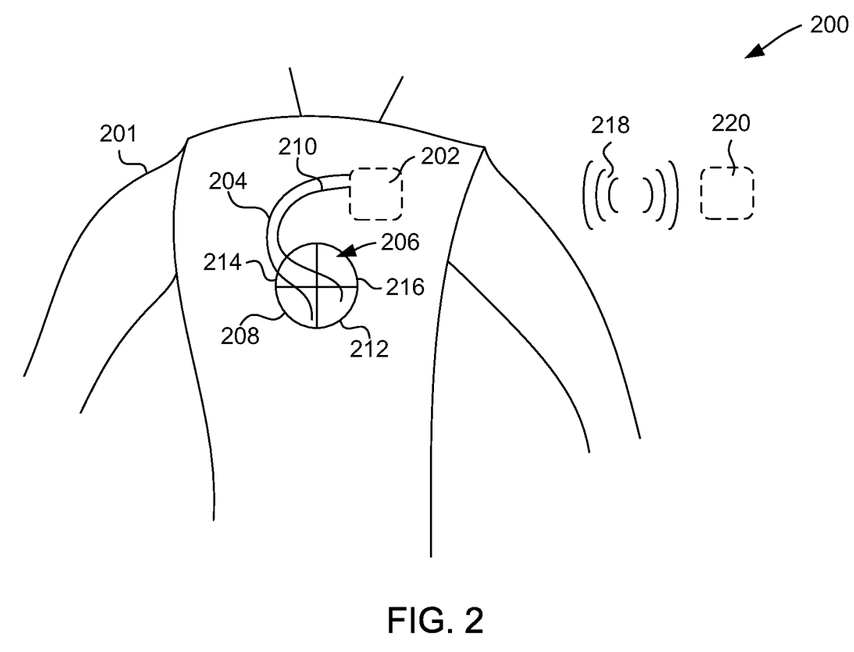
FIG. 2 is an implanted medical system including a battery that includes, but is not limited to, a fluorinated carbon framework defining open areas disposed along three axes, according to some embodiments.

FIG. 2 is an implanted medical system including a battery that includes, but is not limited to, a fluorinated carbon 3D framework, according to certain examples. The system includes a cardiac rhythm management device 202 coupled to a first lead 204 to extend through the heart 206 to the right ventricle 208 to stimulate at least the right ventricle 208. The system also includes a second lead 210 to extend through the heart 206 to the left ventricle 212. In various examples, one or both of the first lead 204 and the second lead 210 include electrodes to sense intrinsic heart signals and to stimulate the heart. The first lead 204 is in direct contact (e.g., touching) with the right atrium 214 and the right ventricle 208 to sense and/or stimulate both of those tissue regions. The second lead 210 is in direct contact with the right atrium 216 and the right ventricle 212 to sense and/or stimulate both those tissue regions. The cardiac rhythm management device 202 uses the lead electrodes to deliver energy to the heart, between electrodes on the leads or between one or more lead electrodes and the cardiac rhythm management device 202. In some instances, the cardiac rhythm management device 202 is programmable and wirelessly communicates 218 programming information with a programmer 220. In certain examples, the programmer 220 wirelessly 218 charges an energy storage device of the cardiac rhythm management device 202. Other stimulation topologies, such as those that stimulate other portions of the body, additionally benefit from the devices and methods disclosed herein.

Figure 3:
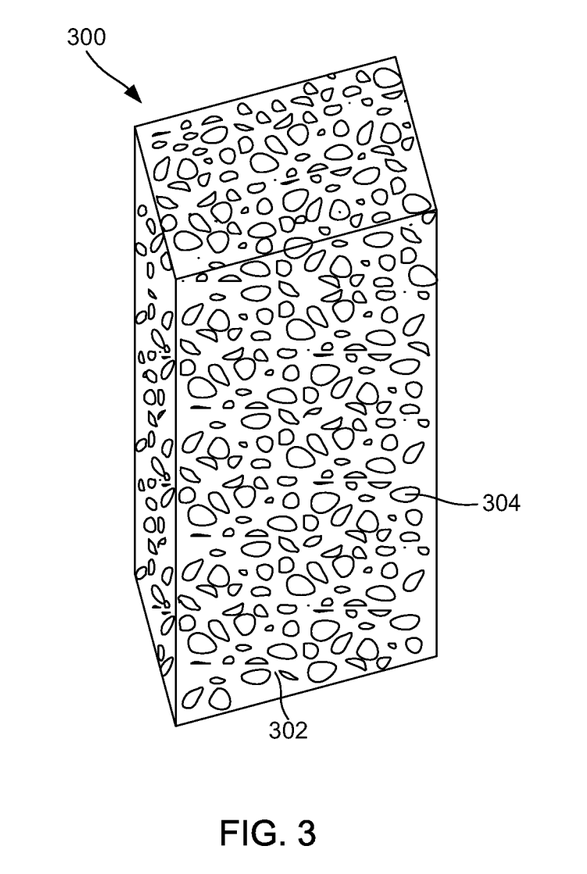
FIG. 3 is a perspective view of a framework defining open areas disposed along three axes, according to various embodiments.
Figure 4:
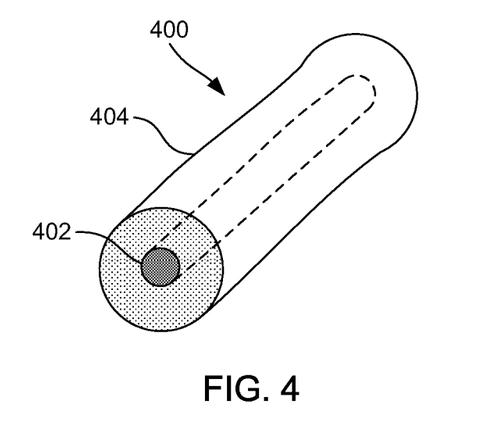
FIG. 4 is a perspective cross-sectioned view of an element of a framework defining open areas disposed along three axes, according to various embodiments.

FIG. 3 is a perspective view of a fluorinated carbon 3D framework, according to various examples. FIG. 4 is a perspective cross-sectioned view of an element of a fluorinated carbon 3D framework, according to various examples. In various examples, a portion of the fluorinated carbon 3D framework 300 includes elements 400 that are fibrous. A conductive portion 402 of the fluorinated carbon 3D framework 300 serves as the current collector in a battery electrode. An active portion 404 is at least partially disposed on an exterior of the elements 400, in certain examples. In some examples, the fluorinated carbon 3D framework 300 is continuous such that an electrical network is formed among a plurality of conductive portions. The electrical network serves as a current collector.

Various examples include, but are not limited to, an active portion that includes solid-gas fluorinated carbon. In various examples, the active portion comprises fluorinated carbon with a formula $CF_x$ in which x is in the range of from about 0.5 to about 0.95. In some instances, the electrode is substantially free of binders. In additional examples, the electrode is substantially free of carbon additives binders.

In certain examples, the fluorinated carbon 3D framework 300 is formed of a carbon foam. In some examples, the foam is open celled. In certain examples, the carbon foam is around 40% porous. In various examples, the fluorinated carbon 3D framework 300 is pliable.

Certain examples include, but are not limited to, a reticulated vitreous carbon ("RVC") foam that is a porous foam material composed of vitreous carbon. In some instances, vitreous carbon is a form of glass-like carbon that combines some of the properties of glass with those of industrial carbons. In some examples, the foam is isotropic in its material properties. In various examples, RVC has a low relative density (3%), high surface area, low resistance to fluid flow, and can withstand very high temperatures in non-oxidizing environments. Examples are provided in a range of pore size grades, from about 5 to around 100 pores per inch.

In various examples, RVC foam is inert over a wide temperature range, and has a low bulk thermal conductivity and high electrical conductivity. Some RVC examples have a rigid geometry that, in certain examples, provides a large surface area and low pressure drop for fluid flow. In some examples, the structure of RVC foam promotes an ability to hold infused materials within controlled porosity ranges.

Present examples provide reduced electrochemical polarization at high rates of discharge. Traditional $CF_x$ cathodes contain a mixture of discrete conductive and insulating particles that have high rate performance limitations due to the insulating nature of $CF_x$. The disclosed electrodes including a fluorinated carbon 3D framework improve high rate discharge by improving the conductivity of the cathode and reducing polarization losses due to ohmic resistance.

The present subject matter reduces heat generation. $CF_x$ electrodes that do not include a fluorinated carbon current collector suffer from a rise in heat when discharged at high rates (e.g., $I^2R$ effects). Electronic conductivity improvements provided by a fluorinated carbon 3D framework lower heat generation at high rates of discharge.

Examples including a fluorinated carbon 3D framework provide a reduced initial voltage delay. The initial voltage delay in traditional $Li/CF_x$ cells is attributed to the poor conductivity of $CF_x$ and a higher activation energy of fluorinated edge groups. Improvements in the electronic conductivity from the fluorinated carbon 3D framework benefit batteries by providing a reduced initial voltage delay.

Various examples benefit from reduced cathode processing. The disclosed CFx electrodes do not necessarily use traditional cathode processing. Traditional cathodes mix of active and inactive components, coating and calendaring to a conductive substrate. The disclosed electrode contains active and inactive components within the network at an improved porosity. The properties of the improved electrode such as loading, thickness, porosity and conductivity are determined during the manufacture of the foam and fluorination of the foam. Accordingly, the overall number of processing steps is reduced.

The present subject matter benefits from reduction or elimination of binder and conductive additives, as the improved electrodes set forth herein do not require additional carbon or binders. The conductive carbon core forms the electronic network for electrons to flow throughout the cathode, and the fluorinated carbon 3D framework forms a rigid bound structure where binders are not needed. In both cases, the absence of binders and carbon allow for a higher percentage of active materials.

In one example, a 1.2 amp hour $MnO_2$ battery having a gravimetric capacity of 308 milliamp hours per gram has a volumetric capacitor of 1540 milliamp hours per cc has a volume of at least 3.91 cubic centimeters. A 2.0 amp hour battery having a similar gravimetric and volumetric capacity has a volume of around 8.64 cubic centimeters.

Contrast $CF_x$ battery examples including a fluorinated carbon 3D framework. Some examples have a gravimetric capacity of 860 milliamp hours per gram has a volumetric capacitor of 2322 milliamp hours per cc has a volume of less than 3.46 cubic centimeters. A 2.0 amp hour battery having a similar gravimetric and volumetric capacity has a volume of less than 6.0 cubic centimeters.

Figure 5:
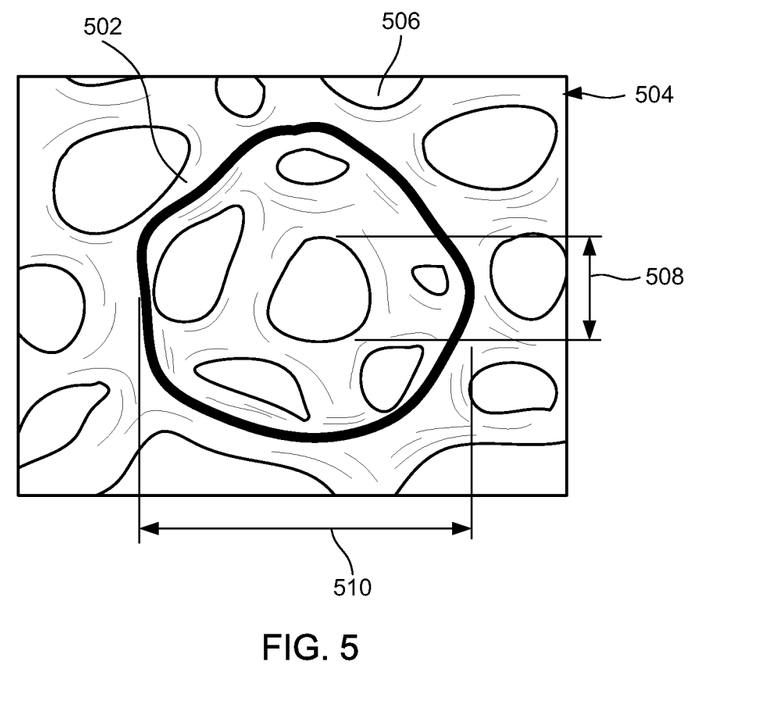
FIG. 5 is a close-up view of a framework defining open areas disposed along three axes, according to some embodiments.

FIG. 5 is a close-up view of a fluorinated carbon 3D framework, according to some examples. In certain examples, the fluorinated carbon 3D framework is formed of foam. In various examples, the fluorinated carbon 3D framework 500 is formed of foam defining open cells 510. A cell 510 is defined by the fluorinated carbon 3D framework 504. The cell, according to various examples, represents a bubble in the foam. Pores 506 provide fluid communication with other cells. Elements 502 define the cell 510.

Figure 6A:
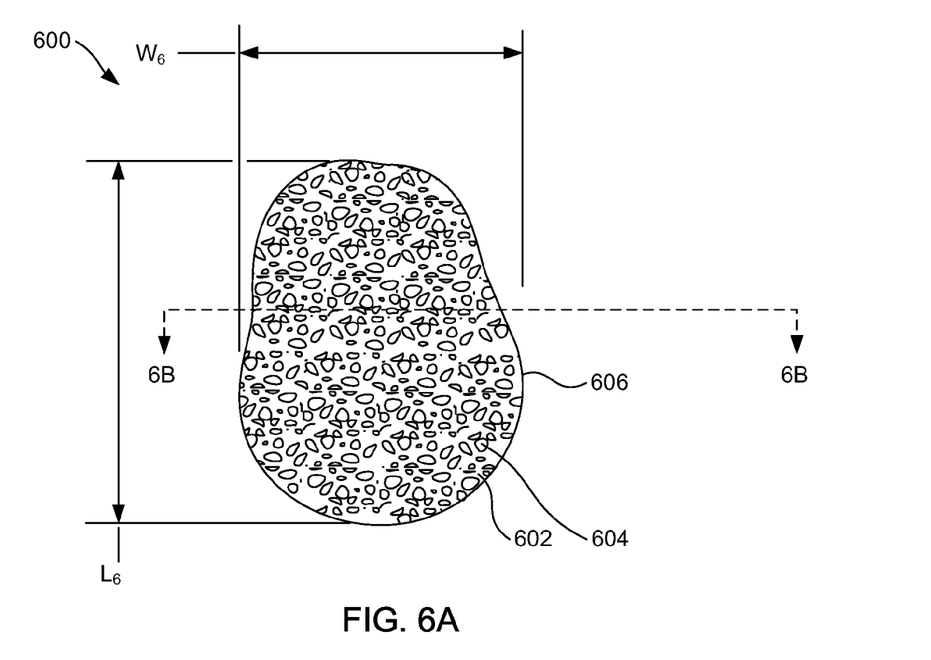
FIG. 6A is a plan view of a framework defining open areas disposed along three axes, according to various embodiments.
Figure 6B:
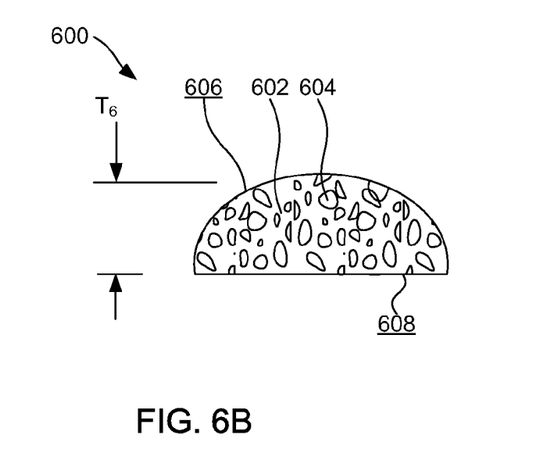
FIG. 6B is a cross section taken along line 6B-6B in FIG. 6A.

FIG. 6A is a plan view of a fluorinated carbon 3D framework 602, according to various examples. FIG. 6B is a cross section taken along line 6B-6B in FIG. 6A. The electrode 600 defines a plurality of pores 604. In some instances, the electrode has an electrode shape 606 that is selected to at least partially mate a battery case shape. In some examples, the electrode 600 is cut, such as by routing or another cutting operation. In certain examples, the electrode has a flat surface 608. In some examples, additional electrodes are stacked onto the flat surface 608. An electrode stack includes a number of electrodes, each including at least one major face that faces a major face of another electrode. In some instances, a plurality of electrodes are disposed in a stack and interconnected with one another. Interconnection is via a conductive interconnect, in certain examples. Examples of an interconnect include, but are not limited to, a weld busbar, rivet, metal spray and the like. Potential electronic connection solutions include, for example, metallic electroplating to a masked portion of the carbon. Accordingly, some examples include masking the carbon foam, fluorinating the unmasked portions, removing the mask and then interconnecting to the portion that was masked. Some examples include an electrical connection through a pressure contact fit to a conductive portion.

In various examples, the width $W_6$ and the thickness $T_6$ are selected such that the electrode 600 conforms to a selected battery case. Examples include a fluorinated carbon 3D framework 602 that is connected to a conductor. In some examples, the electrode 600 is coupled to conductor. A conductor is coupled to the fluorinated carbon 3D framework 602 such that it is electrically and physically coupled to the fluorinated carbon 3D framework 602, in some examples. Example coupling include, but are not limited to, a weld busbar, rivet, metal spray and the like.

Figure 7A:
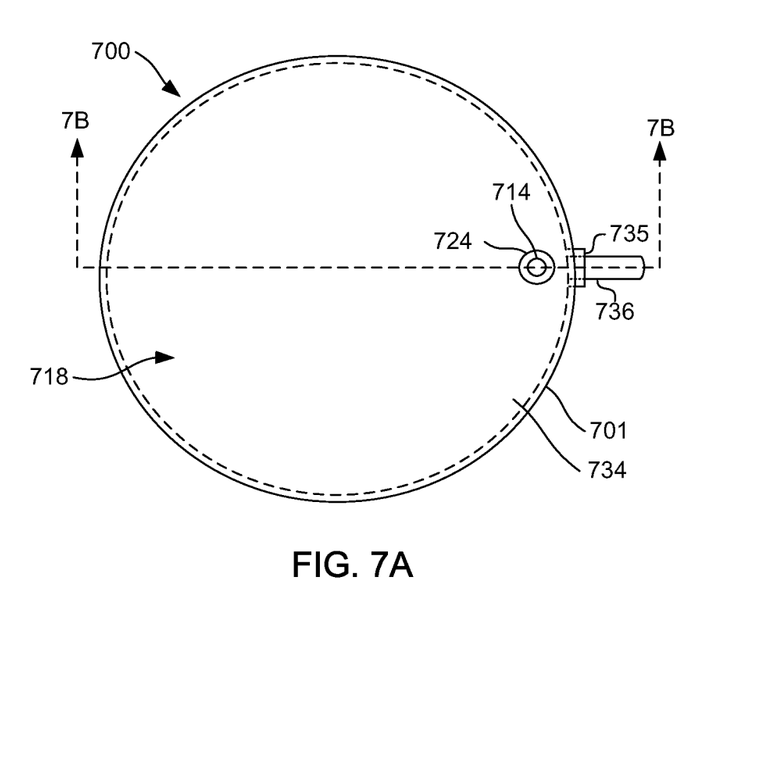
FIG. 7A is a plan view of a battery, according to various embodiments.
Figure 7B:
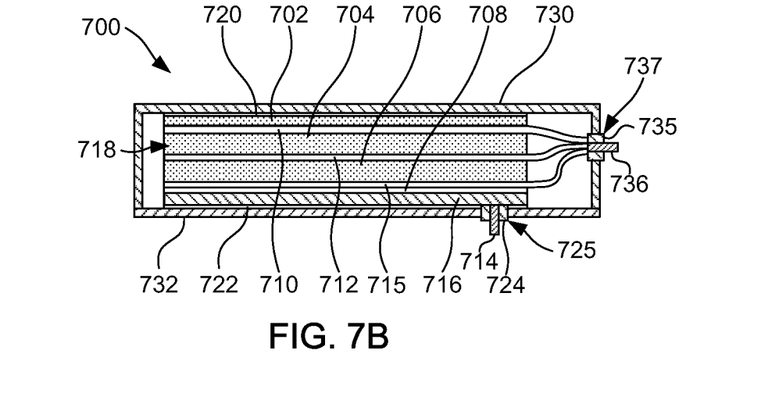
FIG. 7B is a cross section taken along the line 7B-7B in FIG. 7A.

FIG. 7A is a plan view of a battery, according to various examples. FIG. 7B is a cross section taken along the line 7B-7B in FIG. 7A. Various examples include a battery stack 718 disposed in a battery case 701. The battery case 701, in various examples, includes a dish shaped portion 730 and a lid 732, with the lid sealed to the dish shaped portion 730, but the present subject matter is not so limited.

In various examples, the battery stack 718 includes a plurality of electrodes and separator. For example, a first separator 720 is disposed between the case 701 and a first electrode including a 3D framework 702 to physically separate the electrode including a 3D framework 702 from the case 701. In certain examples, the electrode including a 3D framework 702 is coupled to a conductor 710. Some instances include a second electrode including a 3D framework 704 coupled to a conductor 712. Certain examples include a third electrode including a 3D framework 706 coupled to a conductor 715. In certain examples, the first, second and third electrodes abut and are in electrical communication with one another. In additional examples, the first, second and third electrodes abut the battery case 701. In some instances, the first, second and third electrodes are cathodic. In various examples, the stack 718 is a stack of electrodes, each adapted to stack into the stack. An electrode adapted for stacking, in some instances, is prepared in pelletized before stacking.

In certain examples, the first, second and third electrodes are electrically coupled via an interconnection between the first conductor 710, the second conductor 712 and the third conductor 715. Interconnection between the first conductor 710, the second conductor 712 and the third conductor 715 is via a conductive interconnect. Each of the conductors is electrically coupled to a respective 3D framework via welding and the like. In some instances, a conductor is formed of a metallic spray. Certain examples include a metallic ribbon coupled to the 3D framework.

In various examples, a feedthrough 737 including an electrical insulator 735 and a terminal 736 is disposed through the dish shaped portion 730 and placed into connection with the first conductor 710, the second conductor 712 and the third conductor 715 such as by welding.

Various examples additionally include a further electrode 716. In various examples, one or more separators 708 separate the further electrode 716 from additional electrodes, such as the electrode including conductor 715. In additional examples, a separator 722 separates the further electrode 716 from the case 701 such as by separating the further electrode 716 from the lid 732.

In various examples, the first, second and third electrodes are stacked into the dish shaped portion 730. Separator is stacked onto the third electrode, and a further electrode 716 is stacked into the dish shaped portion 730. In various examples, a lid 732 is fixed to the dish shaped portion, with a feedthrough 725 including an electrical insulator 724 and a terminal 714 is disposed through the lid 732 and placed into connection with the further electrode 716 such as by welding. In some examples, the further electrode 716 is welded to the feedthrough prior to fastening the lid 732 to the dish shaped portion 730.

Figure 8:
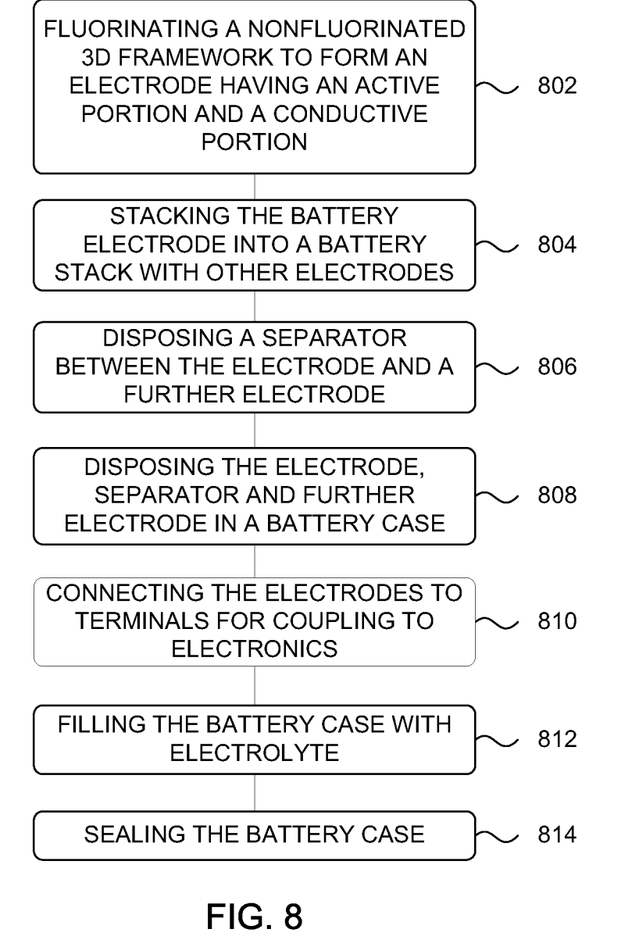
FIG. 8 is a method of making a battery including a framework defining open areas disposed along three axes, according to some embodiments.

FIG. 8 is a method of making a battery including a fluorinated carbon 3D framework, according to certain examples. At 802, the method includes, but is not limited to, fluorinating a nonflourinated 3D framework to form an electrode having an active portion and a conductive portion. At 804, the method includes stacking the battery electrode into a battery stack with other electrodes. At 806, the method includes disposing a separator between the electrode and a further electrode. At 808, the method includes disposing the electrode, separator and the further electrode in a battery case. At 810, the method includes connecting the electrode to terminals for coupling to electronics. Some methods include coupling the terminals to the electronics. At 812, the method includes filling the battery case with electrolyte. At 814, the method includes sealing the battery case.

Figure 9:
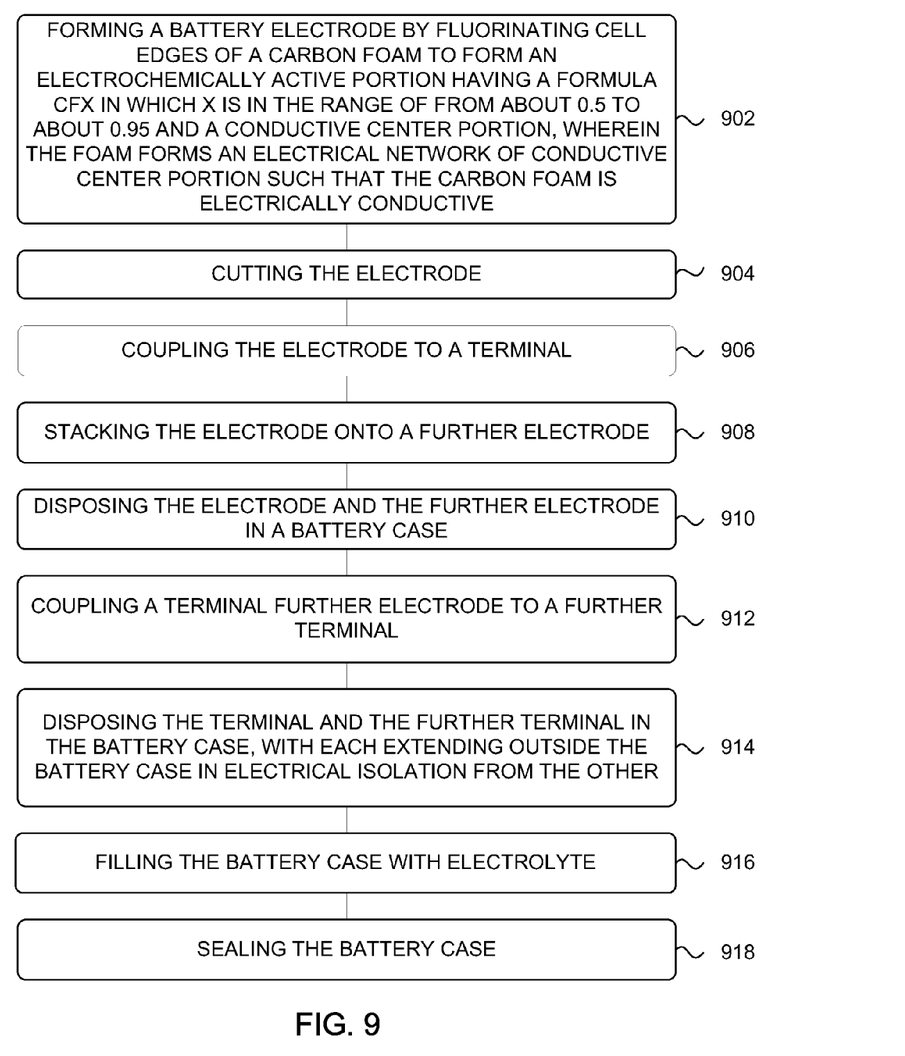
FIG. 9 is a method of making a battery including a framework defining open areas disposed along three axes, according to some embodiments.

FIG. 9 is a method of making a battery including a fluorinated carbon 3D framework, according to some instances. At 902, the method includes forming a battery electrode by fluorinating elements of a carbon foam to form an electrochemically active portion having a formula CFx in which x is in the range of from about 0.5 to about 0.95, with a conductive portion, where the foam forms an electrical network of conductive portions such that the carbon foam is electrically conductive. At 904, the method includes cutting the electrode, such as by routing. At 906, the method includes coupling the electrode to a terminal. In some examples, coupling includes electrically coupling the electrode to a terminal. In certain examples, coupling includes physically coupling the electrode to the terminal. At 908, the method includes stacking the electrode onto a further electrode. At 910, the method includes disposing the electrode and the further electrode in a battery case. At 912, the method includes coupling the further electrode to a further terminal. At 914, the method includes disposing the terminal and the further terminal in the battery case, with each extending outside the battery case in electrical isolation from the other. At 916, the method includes filling the battery case with electrolyte. At 918, the method includes sealing the battery case.

Methods disclosed herein include optional elements. Some methods include an electrode in which an active portion has a formula $CF_x$ in which x is in the range of from about 0.5 to about 0.95. Some methods include fluorinating the carbon foam including fluorinating open cells of the carbon foam. Some methods include cutting an excised electrode from the shaped electrode. Some methods include stacking the other electrodes into the stack such that the stack has a predetermined energy density. Some methods include fluorinating carbon foam that is around 40% porous.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. An apparatus, comprising:
   a battery case sealed to retain electrolyte;
   an electrode disposed in the battery case, the electrode comprising a 3D framework defining open cells within the electrode disposed along three axes, the 3D framework including elements defining the open cells that each include a conductive carbon core at least partially surrounded by a fluorinated carbon electrochemically active portion, wherein a plurality of the conductive carbon cores form an electrically conductive network that serves as a current collector, with each of the conductive carbon cores of each element of the 3D framework being interior to the element's respective surrounding fluorinated carbon active portion of the 3D framework, wherein at least some of the open cells within the 3D framework are in fluid communication with other open cells in the 3D framework via a plurality of pores in the 3D framework;
   a conductor electrically coupled to the electrode and in electrical communication with the electrically conductive network and sealingly extending through the battery case to a terminal disposed on an exterior of the battery case;
   a further electrode disposed in the battery case;
   a separator disposed between the electrode and the further electrode; and
   a further terminal disposed on the exterior of the battery case and in electrical communication with the further electrode, with the terminal and the further terminal electrically isolated from one another.

2. The apparatus of claim 1, wherein the active portion comprises fluorinated carbon with a formula CF, in which x is in the range of from about 0.5 to about 0.95.

3. The apparatus of claim 1, wherein the 3D framework is formed of carbon foam that is vitreous.

4. The apparatus of claim 1, wherein the 3D framework is porous.

5. The apparatus of claim 1, wherein the 3D framework includes a carbon tram defining open cells.

6. The apparatus of claim 5, wherein the carbon foam is around 40% porous.

7. The apparatus of claim 5, wherein the carbon foam is flexible.

8. The apparatus of claim 7, wherein the electrode includes a reticulated vitreous carbon foam.

9. The apparatus of claim 1, wherein the electrode is substantially free of binders.

10. The apparatus of claim 9, wherein the electrode is substantially free of carbon additives binders.

11. A system, comprising:
    a hermetically sealed device housing;
    a battery disposed in the hermetically sealed device housing, the battery comprising:
    a battery case sealed to retain electrolyte;
    an electrode disposed in the battery case, the electrode comprising a 3D framework defining open cells within the electrode disposed along three axes, the 3D framework including elements defining the open cells that each include a conductive carbon core at least partially surrounded by a fluorinated carbon electrochemically active portion, wherein a plurality of the conductive carbon cores form an electrically conductive network that serves as a current collector, with each of the conductive carbon cores of each element of the 3D framework being interior to the element's respective surrounding fluorinated carbon active portion of the 3D framework, wherein at least some of the open cells within the 3D framework are in fluid communication with other open cells in the 3D framework via a plurality of pores in the 3D framework;
    a conductor electrically coupled to the electrode and sealingly extending through the battery case to a terminal disposed on an exterior of the battery case;
    a further electrode disposed in the battery case;
    a separator disposed between the electrode and the further electrode; and
    a further terminal disposed on the exterior of the battery case and in electrical communication with the further electrode, with the terminal and the further terminal electrically isolated from one another; and
    an electronic cardiac rhythm management circuit coupled to the battery and adapted to discharge the battery to provide a therapeutic pulse.

12. The system of claim 11, wherein the device housing has a form factor, and the battery case is shaped to at least partially conform to the form factor.

13. The system of claim 12, wherein the battery case has a case shape, and the electrode is shaped to at least partially mate the case shape.

14. An apparatus, comprising:
    a battery case sealed to retain electrolyte;
    an electrode disposed in the battery case, the electrode comprising a 3D framework defining open cells within the electrode disposed along three axes, wherein the 3D framework includes a 3D framework of conductive carbon core forming an electrically conductive network and serving as a current collector and a 3D framework of fluorinated carbon active electrode material covering the 3D framework conductive carbon core wherein at least some of the open cells within the 3D framework are in fluid communication with other open cells in the 3D framework via a plurality of pores in the 3D framework;
    a conductor electrically coupled to the electrode and in electrical communication with the electrically conductive network and sealingly extending through the battery case to a terminal disposed on an exterior of the battery case;
    a further electrode disposed in the battery case;
    a separator disposed between the electrode and the further electrode; and
    a further terminal disposed on the exterior of the battery case and in electrical communication with the further electrode, with the terminal and the further terminal electrically isolated from one another.

15. The apparatus of claim 14, wherein the 3D framework includes a carbon foam defining open cells.

16. The apparatus of claim 15, wherein the carbon foam is around 40% porous.

17. The apparatus of claim 15, wherein the carbon foam is flexible.

18. The apparatus of claim 15, wherein the electrode includes a reticulated vitreous carbon foam.

19. The apparatus of claim 14, wherein the electrode is substantially free of binders.

* * * * *